United States Patent
Nicolella et al.

(10) Patent No.: US 11,721,437 B2
(45) Date of Patent: Aug. 8, 2023

(54) DIGITAL TWIN FOR PREDICTING PERFORMANCE OUTCOMES

(71) Applicant: Southwest Research Institute, San Antonio, TX (US)

(72) Inventors: Daniel P. Nicolella, San Antonio, TX (US); Kase J. Saylor, San Antonio, TX (US); Mark J. Libardoni, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 1041 days.

(21) Appl. No.: 16/429,024

(22) Filed: Jun. 2, 2019

(65) Prior Publication Data

US 2019/0371466 A1 Dec. 5, 2019

Related U.S. Application Data

(60) Provisional application No. 62/680,215, filed on Jun. 4, 2018.

(51) Int. Cl.
*G16H 50/20* (2018.01)
*G06T 17/00* (2006.01)
*G06F 30/20* (2020.01)

(52) U.S. Cl.
CPC .............. *G16H 50/20* (2018.01); *G06F 30/20* (2020.01); *G06T 17/00* (2013.01)

(58) Field of Classification Search
CPC .......... G16H 50/20; G06F 30/20; G06T 17/00
See application file for complete search history.

(56) References Cited

U.S. PATENT DOCUMENTS

| 2019/0198169 A1* | 6/2019 | T ............................ G16H 50/50 |
| 2019/0321553 A1* | 10/2019 | Grosman ............... G16H 40/63 |
| 2019/0355447 A1* | 11/2019 | Barkol .................. G06F 3/0484 |

OTHER PUBLICATIONS

Feng, Y., Chen, X., & Zhao, J. (Jan. 19, 2018). Create the individualized digital twin for noninvasive precise pulmonary healthcare. Significances Bioengineering & Biosciences, 1(2). (Year: 2018).*
Peruzzini, M., Grandi, F., & Pellicciari, M. (2017). Benchmarking of tools for user experience analysis in industry 4.0. Procedia manufacturing, 11, 806-813. (Year: 2017).*

* cited by examiner

*Primary Examiner* — Bijan Mapar
(74) *Attorney, Agent, or Firm* — Livingston Law Firm

(57) ABSTRACT

A method of generating a digital twin and of using the digital twin to predict activity of an animate subject. The digital twin is generated from at least system model data and movement data. The digital twin can be activated to simulate a specified activity that the subject is performing or will perform. If desired, the subject can be instructed to perform the same activity while wearing at least one wearable sensor, which is applied to the digital twin. Using artificial intelligence techniques, the activity simulation predicts one or more physical outcomes from the activity.

4 Claims, 6 Drawing Sheets

DIGITAL TWIN FOR PREDICTING PERFORMANCE OUTCOMES

PRIORITY TO PROVISIONAL FILING

This application claims the filing date benefit of U.S. Prov. App. No. 62/680,215, filed Jun. 4, 2018, entitled "Digital Twin for Monitoring Human Activity and Predicting Performance Outcomes".

TECHNICAL FIELD OF THE INVENTION

This invention relates to performance prediction of animate beings, and more particularly to creation of a digital twin for an animate being.

BACKGROUND OF THE INVENTION

The human body is a highly complex system whose functioning is the result of the simultaneous and often synergistic expression of a large number of individual and interrelated traits (e.g., physical, physiological, and psychological). As a result, human performance is an integrative function of many complex and interrelated characteristics such as the individual's specific anatomic structure, the size, shape, attachment points, and neuromuscular coordination of the muscles required to generate motion, the microstructural organization of each muscle, laxity (or lack thereof) in ligaments, the individual's metabolic efficiency and capacity, perceived pain, fatigue, and multiple neuropsychological factors, just to name a few.

Co-adaptations of these factors provide for combinations of traits through which an individual can achieve "nominal" human performance. For example, individuals with vastly different body structures and neuromuscular coordination can achieve the same performance on a three-mile run with different combinations of traits. In other words, significantly different complex patterns of individual traits can result in similar levels of performance. Furthermore, a subset of these trait combinations expressed by specific individuals, although sufficient for nominal functional performance, could be sub-optimal if the individual is subjected to atypical or high-performance training regimes or extreme operational environments. Consequently, sub-optimal performance, overt performance failures, and increased risk of injury can result from multiple, distinct combinations or patterns of individual traits that are not manifest until individuals are stressed during training environments.

The current approach to monitoring human performance is to measure a relatively small number of variables and compare these variables to "population norms" to determine the health and readiness of the individual. Although this approach is straightforward, the disadvantages to this approach are the a priori selection of variables and the uni-variate nature in which the variables are analyzed, which generally do not account for the interrelatedness and synergistic effect of the system as a whole. Differences between and within operators may not be detectable or raise concerns but can often result in a decline in performance that may lead to an increased risk of injury, or other adverse outcomes. Individuals who express subtle, yet suboptimal trait patterns may "fly under the radar" and go undetected using conventional performance assessment techniques until it is too late, often resulting in injury or performance failures.

DETAILED DESCRIPTION OF THE INVENTION

The following description is directed to performance prediction that is based on a digital twin, customized to an individual. The individual is a human for purposes of example herein, but the same concepts may be applied to any animate subject. The performance may be various activities of the subject, whether actively initiated by the subject, such as athletics, or passive, such as the subject's health.

The system combines individualized neuromusculoskeletal modeling, non-invasive metabolic state monitoring, full or partial body medical imaging, full or partial body finite element and/or other physics-based modeling, with specific human system state sensing (heart rate variability, temperature, muscle oxygenation, etc.) into a digital representation of an individual. The result is a "digital twin" of the individual that can be directed to have dynamic states. This digital twin can then be used to inform training, nutrition, rest, and recovery protocols to optimize individual performance, reduce injuries, and increase operational readiness.

An advantage of the digital twin is that it helps achieve optimal human performance, facilitating control of interactions between an individual's many traits and processes. For any individual, subtle changes in one or a few traits or behaviors affect changes in a multitude of other outcomes due to the interrelatedness and synergistic nature of the human system. Consequently, an individual may respond differently to training, nutrition, stress, rest, recovery, etc., with individuals falling within a continuum of high responders to non-responders. As such, each individual may require customized training protocols, requirements, rest, sleep requirements, etc., to achieve and maintain optimal levels of operation performance.

Figure 1:
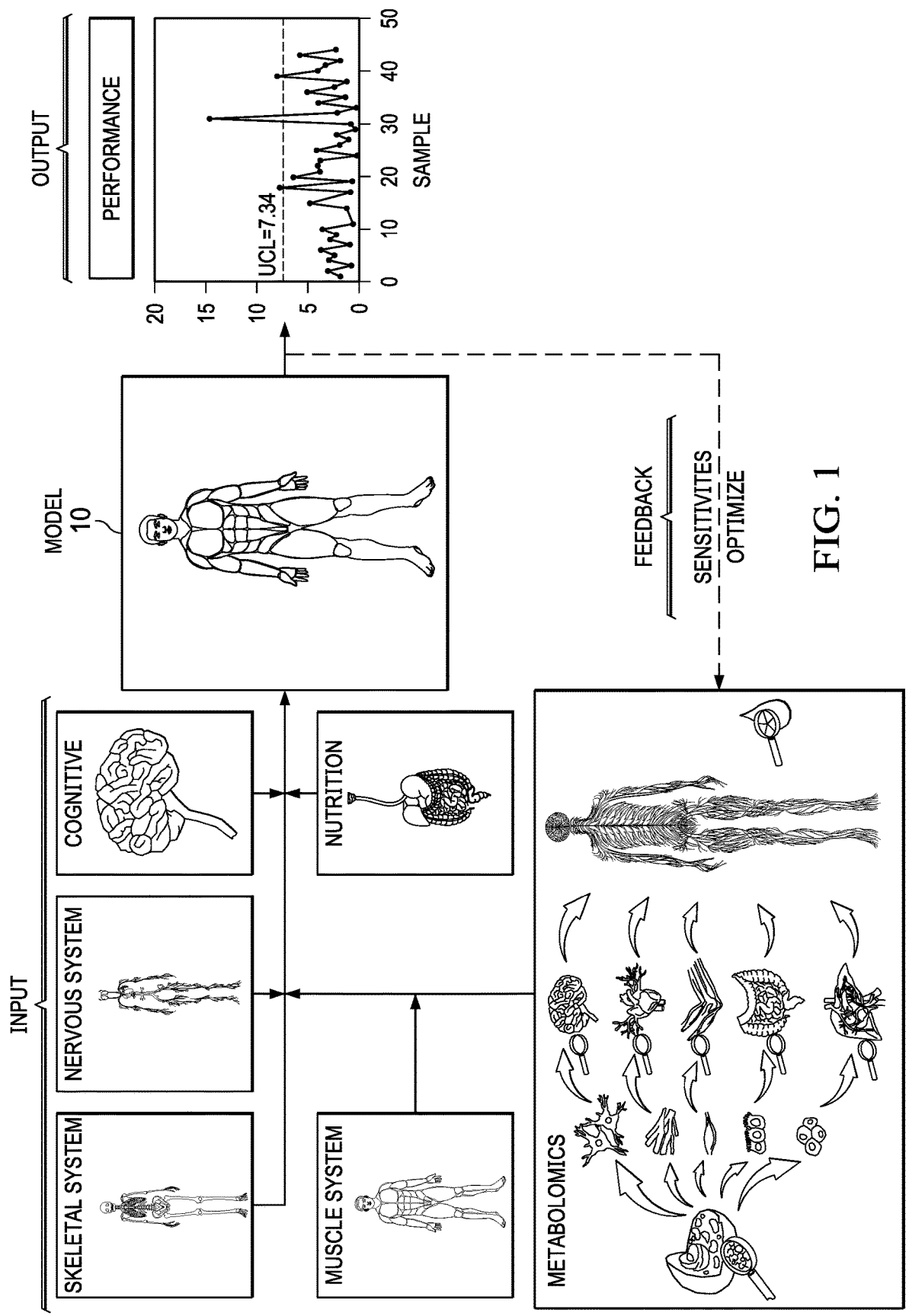
FIG. 1 illustrates a display of a digital twin and its inputs.

FIG. 1 illustrates a human digital twin 10, generated in accordance with the invention. The digital twin 10 is implemented using computer hardware and software, programmed to perform the tasks described herein.

The input to the digital twin is various types of conventionally collected human system data, as well as motion capture data. Examples of the input data is data from conventional wearables, blood and urine biomarkers, etc. This data is processed in an integrative, multivariate, learning machine, which is trained to act as a digital twin 10.

The digital twin is a physics-based digital representation of the individual. It simulates what the human would experience under specific external and/or internal conditions. The simulation results, along with data from things such as wearable sensors, blood analyses, breath metabolomics, are then used within a data analytics framework to capture the "state" of the individual (either a static state or temporal state).

The digital twin can be a finite element model, computational fluid dynamics model, combined fluid-structural model, or other models. As an example, it can be used to simulate any movement by activating muscles to produce force, to produce motion, that then results in cartilage deformation and stress, which may lead to joint degeneration over time. By altering muscle activation patterns, restricting motion via a brace, or other activity modifications, the stress in the individual's cartilage may be reduced, minimizing their likelihood of joint damage.

The digital twin 10 may be used to provide feedback to the subject, coaches, instructors, physicians, or others, that can be used to modify training, nutrition, rest, and recovery to maximize performance and minimize injury.

Digital Twin Input

As stated above, input data for the human digital twin may be data collected from a variety of sources, such as body worn sensors (e.g. accelerometers, heart rate sensors, respiration rate sensors, magnetometers, inertial measurement units, etc.) and biological measurements, such as blood and urine biomarkers. Other input data may be imaging data such as medical imaging data and markerless motion capture data.

Specific input data may include:

a. Physiologic/biologic data: sleep parameters, nutrition, heart rate and heart rate variability, skin and core temperature, sweat, and other biomarkers (e.g. extracted from blood and urine samples).

b. Movement data: accelerometer data, GPS derived movement data, inertial measurement units, etc.

c. Cognitive/psychological data: psychological profiles, questionnaires, etc.

d. High fidelity medical imaging: full or partial body quantitative computed tomography (QCT or CT), full or partial body magnetic resonance imaging (MRI), x-rays, ultrasound, etc.

e. Neuromusculoskeletal biomechanics data: A component of the digital twin is a neuromusculoskeletal computational model customized to the individual. The model measures and assesses time varying internal neuromuscular control and output during movement (e.g. prescribed training exercises, daily activities, etc.). A markerless motion capture system is used to non-invasively and unobtrusively measure physical movement and provide input to the individualized physics-based neuromusculoskeletal dynamics model to measure internal loads, physiologically based muscle outputs (force, power, etc.).

Figure 2:
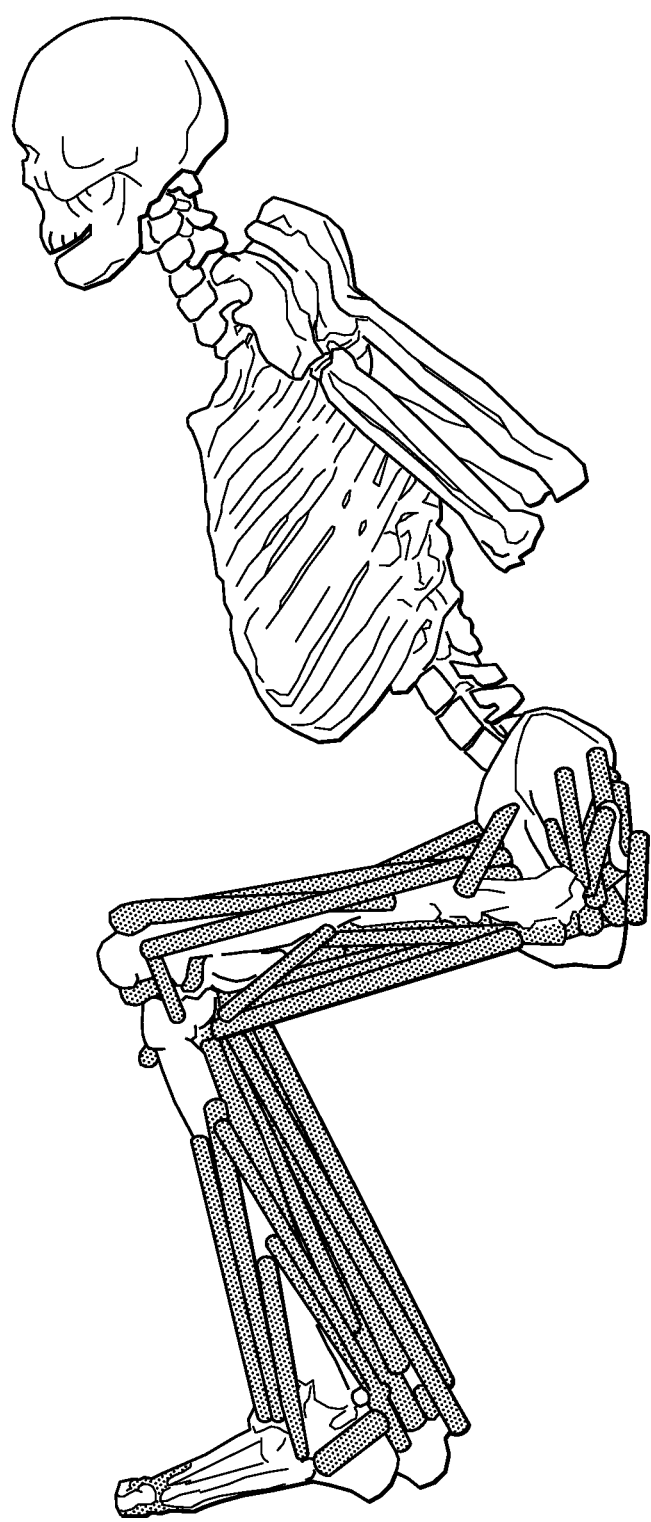
FIGS. 2-4 illustrate a display of a digital twin and its outputs when activated, with muscle activation and joint activation, respectively.
Figure 3:
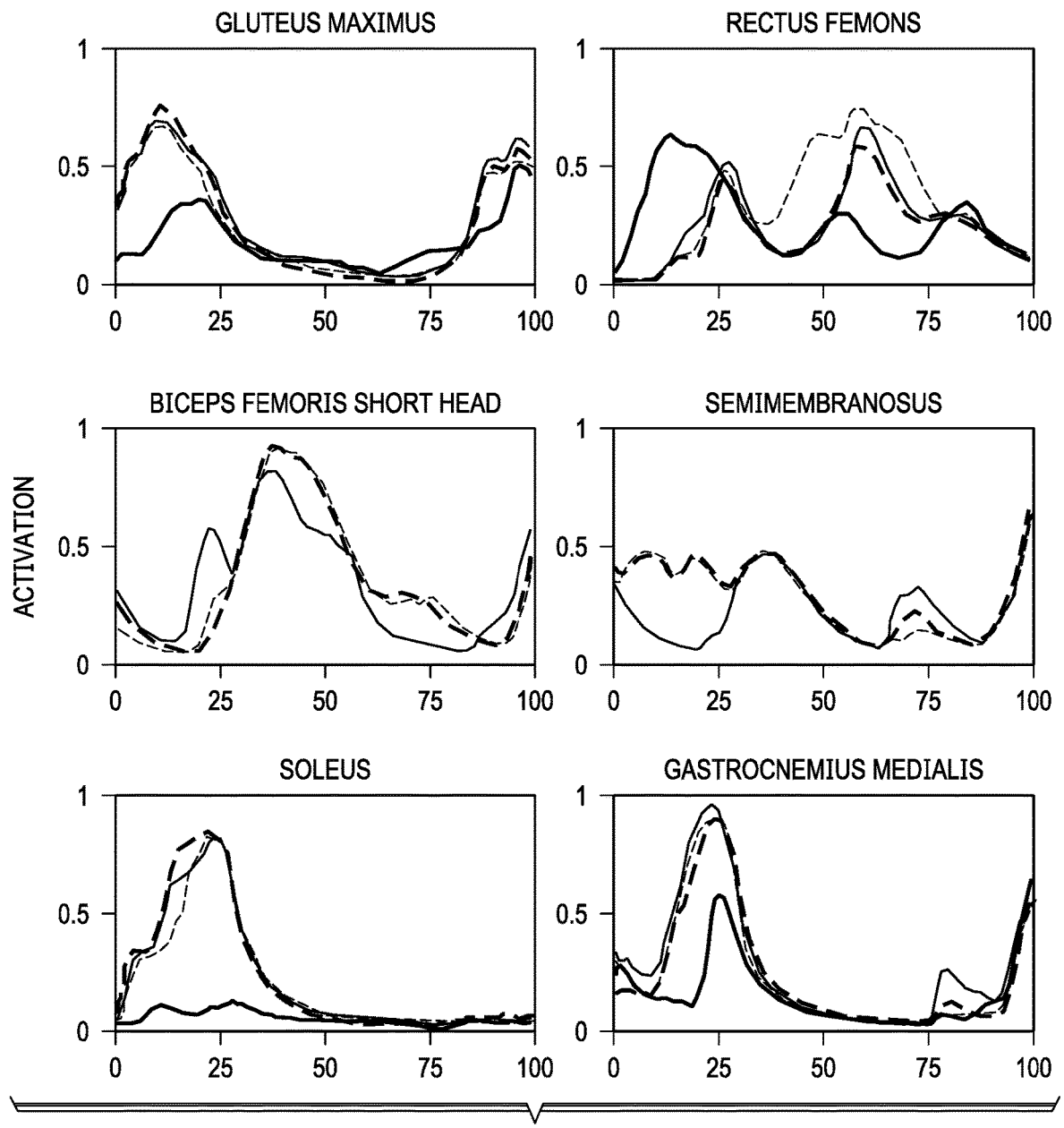
Figure 4:
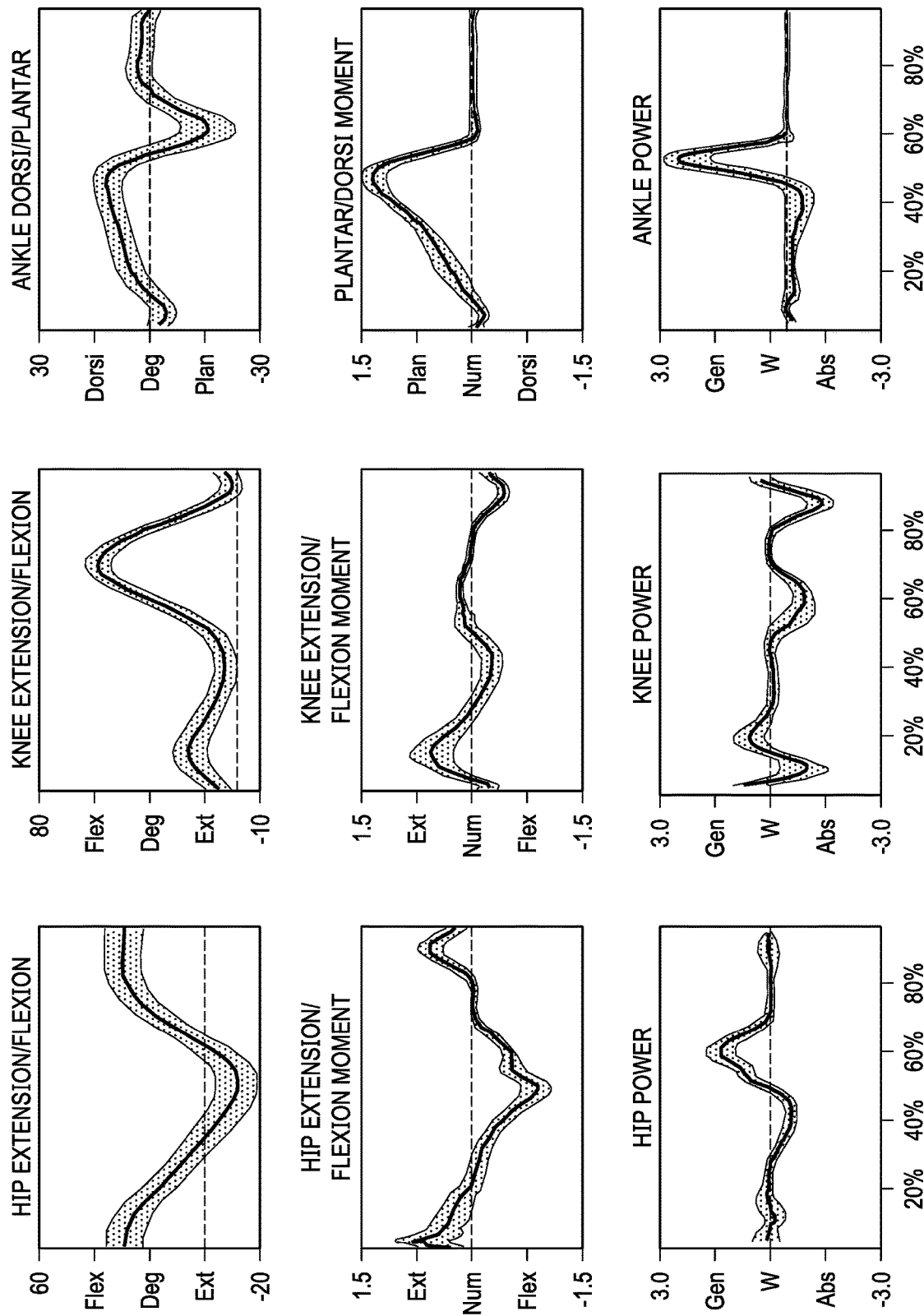

FIGS. 2-4 illustrate an example of a digital twin, and output data available from the digital twin. FIG. 2 illustrates the digital twin, FIG. 3 illustrates muscle activation output, and FIG. 4 illustrates joint kinematics and kinetics output. Activation of muscles can be quantified over time. Output from the neuromusculoskeletal model is processed through the digital twin 10.

f. High fidelity finite element (FE) model data: Data derived from high fidelity FE or other physics-based models (e.g. computational fluid dynamics, electromagnetic models, etc.) of the whole or partial human body.

g. Integrated "omics:" "Omics" collectively refers to the system biology of living organisms by incorporating data across Genomics, Proteomics and Metabolomics. By studying various genes, proteins, and small molecule metabolites an in-depth approach to personalized performance, recovery, and injury prevention can be gleaned from the resulting data. Data obtained via the following "omics" can be processed through the digital twin.

1. Genomics: (cheek swab) Whole genome sequence (WGS) on select or all participants. Conceptually, the WGS contains information about athletic ability and intrinsic response to exercise and other training regimen.

2. Transcriptomics: (blood sample) A measurement of the activity of all genes simultaneously by quantifying the amount of RNA of all genes in a tissue. This provides information about the activity of cells and tissues, including their changes in response to exercise and other stimuli.

3. Metabolomics: (non-invasive breath collection, urine and/or blood). Metabolomics provides a unique snapshot of the chemical process in a sample at a given time point. Multiple sampling points provide a unique system response pattern.

Group Performance Metrics Using Digital Twins

The digital twin is a combination of one or more physics-based models of an individual's body systems and advanced machine learning/artificial intelligence to analyze and process data collected from the individual. The sensor and measurement input data are processed through analysis layers of the digital twin to produce a multivariate human performance metric.

Figure 5:
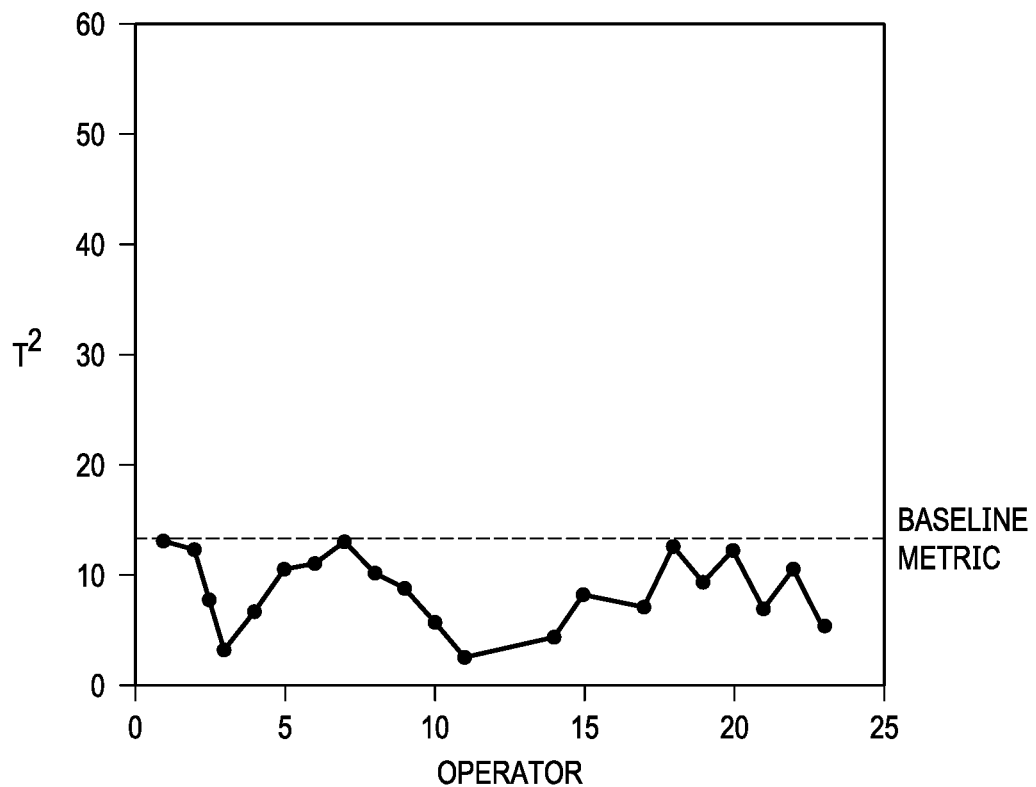
FIG. 5 illustrates the use of digital twins from multiple persons to establish a baseline for a specified activity.

FIG. 5 illustrates an example of a human performance metric collected from a number of digital twins from different subjects, referred to as "operators". A baseline performance zone can be determined from an analysis of historical data from multiple subjects.

Data analysis within the digital twin is accomplished using a variety of methods including statistical analysis, machine learning, artificial neural networks, and physical based modeling. For example, for a given activity, baseline historical data is collected and processed from a subset of subjects who successfully complete a target activity. Examples of such activities are those in military training programs or sports training camps. Each data point is a multivariate representation of the data collected at each time point for each subject. The underlying multivariate data (digital twin input data) represents nominal subject performance with no injuries, performance failures, or other adverse effects. Bounds of nominal performance are determined using the historical data set.

This process is then used to monitor the real-time performance of each individual using the performance metric produced by the multiple digital twins. This will define the nominal human performance zone and will be used to monitor and assess subject performance. A subject whose performance metric is above this limit during training performance monitoring is at risk of performance failure or injury.

An example of the performance metric process is the application of a multivariate statistical process control methods to human performance data. This includes using Hotelling's T2 method to detect combinations of traits or variables that may indicate a significant increase in risk of a future occurrence of an adverse event (e.g., injury). Possible refinements to this method include the incorporation of an exponentially weighted moving average (EWMA) statistic and the Mason-Tracy-Young decomposition. The latter procedure allows the identification of the underlying traits within the multivariate measure that have the greatest influence on an over-limit signal. Additional analysis procedures designed to increase the sensitivity of detection of adverse training effects are variable reduction methods such as principle components analysis, independent components analysis, partial least squares techniques, and deep convolutional networks.

Assessment of human performance with sensitivity analysis and feedback for system optimization may be accomplished using an individual's digital twin. The performance state of each individual is monitored as he or she progresses through an activity, using the digital twin. Deviations outside the nominal performance zone indicate a potential imminent adverse event such as an injury, performance failure or elimination.

Figure 6A:
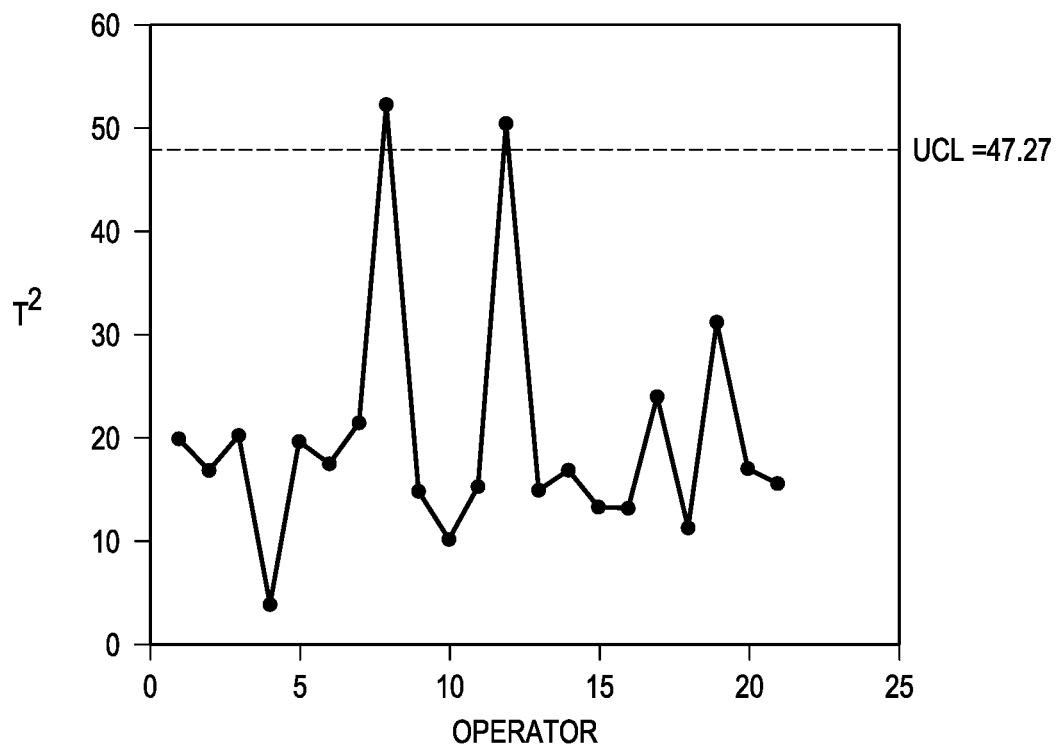
FIGS. 6A and 6B illustrate the use of digital twins to identify persons at risk during a specified activity.
Figure 6B:
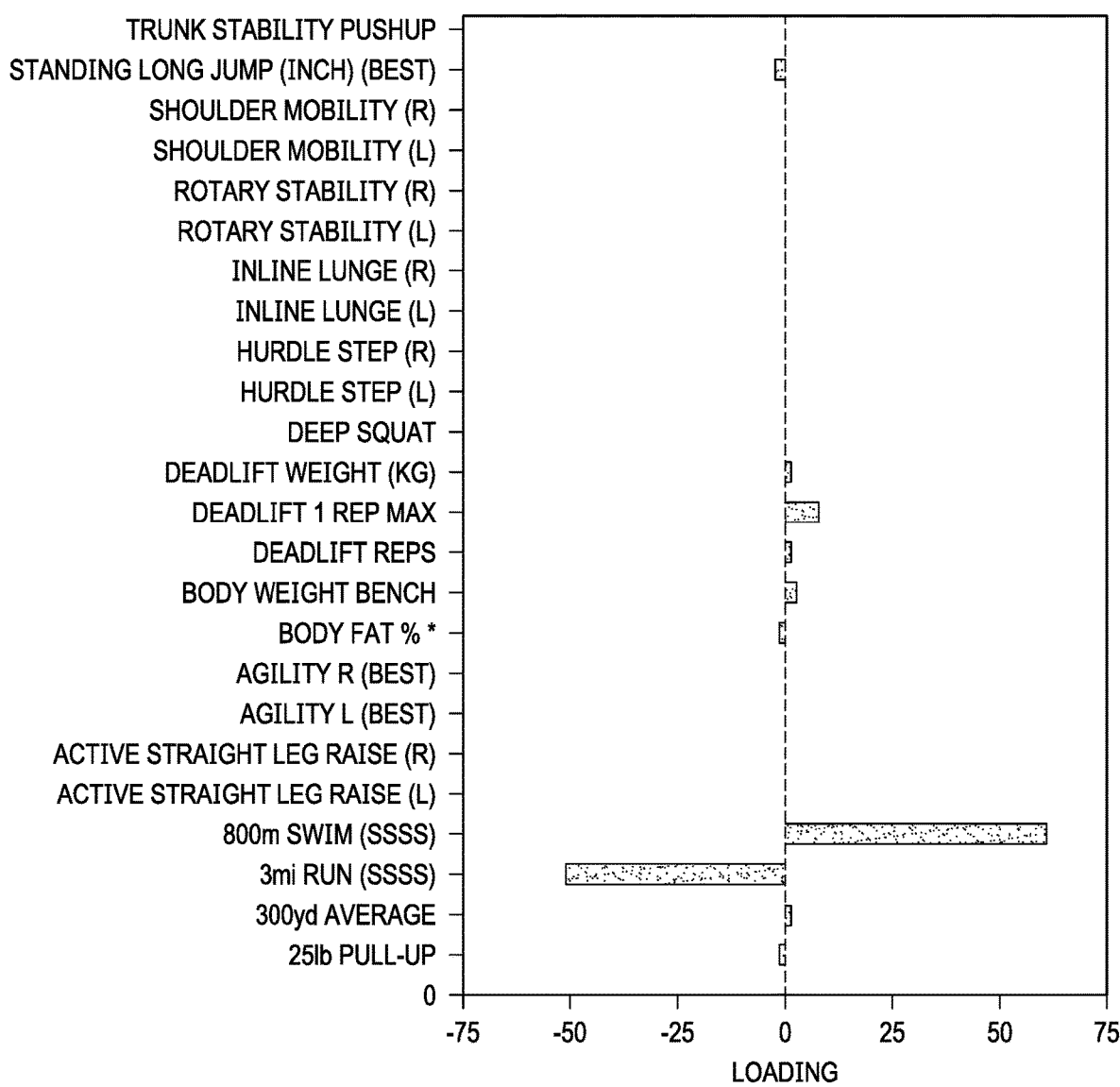

FIG. 6 illustrates an example of monitoring a series of activities for a number of subjects, using their digital twins. Each operator is represented by their own digital twin. FIG. 6A indicates a composite "score" derived using data analytics from output of the digital twin, data from other wearable sensors, and any other data for each individual that is being collected. FIG. 6B is a breakdown of the composite score that indicates how each of the data sources within the composite score is driving it magnitude (i.e. these are sensitivities).

Subject 8 and Subject 12 (also referred to as operators) signal outside the nominal human performance range. Decomposition of the performance signal/metric indicates that Subject 12's performance in two activities are primarily driving the potential future performance failure. Instructors and other personnel can then use this information to attempt to make appropriate corrections to move the subject within the nominal human performance zone.

Individual Performance Prediction

Figure 7:
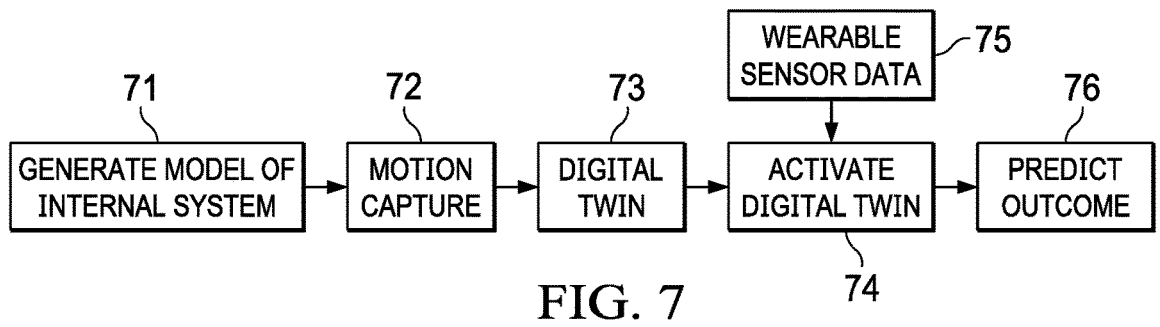
FIG. 7 illustrates a method of generating and using a digital twin to predict outcome of a person engaged in a specified activity.

FIG. 7 illustrates a method of creating and using a digital twin. The digital twin is generated, activated, and used to predict the outcome of a specified behavior that its subject is or will perform.

Step 71 is generating a physics-based model of an animate subject. The data to create this model may be obtained from any of the above-described imaging techniques. Many medical imaging techniques are now available such as x-rays or various imaging scans such as CT or MRI scans. This imaging data is referred to herein as "internal imaging data" because it is used to pictorialize internal elements of the animate subject, such as muscles, bones, and organs. Example of such models are models of the musculoskeletal, nervous, circulatory, respiratory, and gastrointestinal systems, and any combination of these.

Step 72 is using a motion capture system to capture data representing the movement of the subject. The motion capture system may be any one of known marker or markerless motion capture systems. An example of a suitable motion capture system is described in U.S. patent application Ser. No. 15/982,691, filed May 17, 2018, incorporated herein by reference.

Step 73 is combining the model data, the motion capture data, and to generate a digital twin of the subject. This digital twin is a digital image of the subject that can be viewed on a computer screen and programmed to move in specified ways and in specified environments.

Step 74 is activating the digital twin to perform a simulated activity. If desired, Step 74 can be performed in conjunction with the subject performing the same activity, wearing wearable sensors, as indicated by Step 75.

Step 76 is using the digital twin to inform future activity of the subject. The digital twin data is processed with artificial intelligence techniques to predict future outcomes. Examples of future activity could be athletic performance, tactical (military) performance, or career performance of the subject. Future activity could also be "passive" activity that the subject would not otherwise control, such as illness and disease.

The invention claimed is:

1. A method of monitoring activity of an animate real-time subject, comprising:
    generating a digital model for each of a control group of subjects, using internal imaging data obtained from the subjects;
    wherein each model represents at least a model of the subject's internal musculoskeletal system;
    collecting movement data of the subjects, using a motion capture system applied to the subjects;
    combining the model and the movement data, thereby generating a dynamic digital twin of the subjects;
    activating each digital twin to perform a specified physical activity;
    wherein the activating step includes at least activating muscles of the musculoskeletal system of the digital twin to produce motion of the digital twin to perform the physical activity;
    identifying which subjects of the control group of subjects successfully complete the physical activity as measured from data collected from the digital twins of the control group of subjects thereby identifying a subset of nominal performance digital twins having nominal performance data;
    collecting actual activity data of the real-time subject, using at least one wearable sensor worn by the subject during the same physical activity as in the activating step;
    comparing the actual activity data to the nominal performance data; and
    determining if the actual activity data exceeds a threshold of the nominal performance data.

2. The method of claim 1, further comprising modifying the specified activity based on the result of the comparing and determining steps.

3. The method of claim 1, wherein the determining step is performed to evaluate risk of physical injury to the subject.

4. The method of claim 1, wherein the determining step is performed to evaluate risk of injury or disease of the subject.

* * * * *